United States Patent [19]

Hwang et al.

[11] Patent Number: 5,782,769
[45] Date of Patent: Jul. 21, 1998

[54] ULTRASONIC DIAGNOSTIC IMAGE FLASH SUPPRESSION TECHNIQUE

[75] Inventors: Juin-Jet Hwang, Mercer Island; Lauren S. Pflugrath, Seattle, both of Wash.

[73] Assignee: Advanced Technology Laboratories, Inc., Bothell, Wash.

[21] Appl. No.: 876,384

[22] Filed: Jun. 12, 1997

Related U.S. Application Data

[63] Continuation-in-part of Ser. No. 672,782, Jun. 28, 1996, Pat. No. 5,722,412.

[51] Int. Cl.$^6$ ............................................. A61B 8/00
[52] U.S. Cl. ................................................. 600/454
[58] Field of Search ..................... 1/1; 600/442, 441, 600/443, 446, 447, 453, 454, 456, 457, 458; 382/128, 131, 130

[56] References Cited

U.S. PATENT DOCUMENTS

| | | | |
|---|---|---|---|
| 5,197,477 | 3/1993 | Peterson et al. | 128/661.08 |
| 5,413,105 | 5/1995 | Forestieri | 128/660.05 |
| 5,594,807 | 1/1997 | Liu | 382/128 |
| 5,697,372 | 12/1997 | Hughes | 1/1 |

Primary Examiner—George Manuel
Attorney, Agent, or Firm—W. Brinton Yorks, Jr.

[57] ABSTRACT

A flash suppresser for a diagnostic ultrasonic imaging system which processes Doppler signals is provided which eliminates flash artifacts by means of a min-max filter.

22 Claims, 6 Drawing Sheets

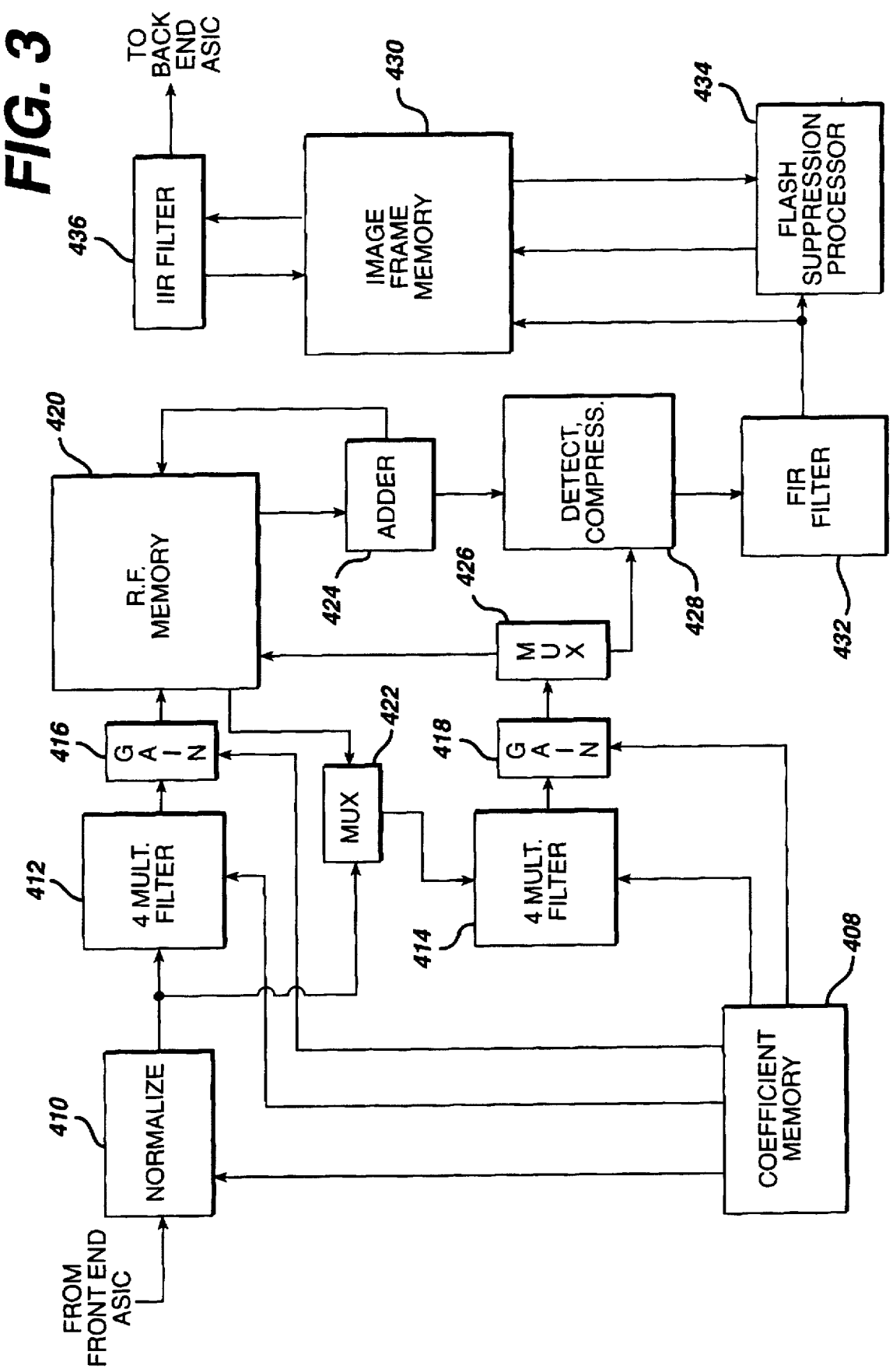

ULTRASONIC DIAGNOSTIC IMAGE FLASH SUPPRESSION TECHNIQUE

This is a continuation-in-part of U.S. patent application Ser. No. 08/672,782, filed Jun. 28, 1996, now U.S. Pat. No. 5,722,412.

This invention relates to medical ultrasonic diagnostic imaging systems and, in particular, to a technique for eliminating flash artifacts from a Doppler image sequence.

Ultrasonic Doppler scanning is a useful diagnostic tool for assessing conditions in the body which have a motional component, such as flowing blood and moving heart walls and valves. As is well known, the Doppler technique relies on the basic Doppler principle, whereby a received echo exhibits a phase or frequency shift in proportion to the motion of the cells which returned the echo. A number of methods have been devised for producing the Doppler information for the physician, including audible tones, spectral displays, and two and three dimensional displays of motion-encoded pixels such as colorflow Doppler images.

The Doppler technique as practiced in ultrasound makes a relative measure of motion, not an absolute one. That is, the motion that is encoded in the received Doppler signal is the relative motion between the cells in the body and the ultrasound transducer. A consequence of this fact is that a Doppler signal is produced, not only when cells in the body are flowing or moving, but also when the transducer moves. In that event, there is relative motion between stationary cells and the moving transducer, which manifests itself as a Doppler return. Additionally, motional effects which are of no interest to the physician, such as chest motion during breathing or the movement of the heart within the chest cavity, will also produce Doppler return signals. These unwanted Doppler return signals can be quite strong in comparison to the desired Doppler signals, such as the relatively weaker signals returned from flowing blood cells. The strong signals can manifest themselves as sudden and significant changes, or "flashes", in the displayed Doppler information. It is therefore desirable to remove these undesired signals so that the Doppler information presented to the physician is uncontaminated with disruptive, unwanted artifacts.

Fortunately, a number of techniques have been developed for eliminating these flash artifacts. U.S. patent [application Ser. No. 08/489,258; issue fee paid] teaches how to eliminate flash artifacts from a spectral Doppler display. U.S. Pat. No. 5,197,477 teaches how to discriminate for and then eliminate flash artifacts from Doppler signals at an early stage in their processing, even before the signals have been formatted for display. It is also possible to eliminate flash artifacts later in the signal processing path, after the Doppler signals have been spatially delineated for display purposes.

One consideration as to the appropriateness of a flash suppression technique is the implementation requirements. This is true when the ultrasound system is miniaturized to a greatly reduced size, and especially so when the entire ultrasound system is compacted into a scanhead-sized unit, as described in the parent application. Such a hand-held ultrasound instrument must be implemented in very small integrated circuit form to reduce size and power requirements, but still must be held to the standards of full-sized premium ultrasound systems so as to retain as many of the features of today's sophisticated ultrasound systems as possible, including full Doppler capabilities.

In accordance with the principles of the present invention, a flash suppression technique is provided for a diagnostic ultrasound system which utilizes a min-max filter. The min-max filter of the preferred embodiment can operate upon temporal Doppler signals even after they have been formatted for display, thereby eliminating the requirement to operate at the higher data rates usually found at earlier stages of the signal processing path. With reduced processing demands, the min-max filtering technique lends itself well to implementation in integrated circuit form, and is especially well suited for use in a hand-held ultrasound instrument as shown in the preferred embodiment. In the preferred embodiment the ultrasound system, from the transducer through to a video output, is fabricated on four types of application specific integrated circuits (ASICs): a transmit/receive ASIC which is connected to the elements of an array transducer, a front end ASIC which performs and controls transmit and receive beamforming, a digital signal processing ASIC which provides processing of the ultrasound signals including min-max filtering, and a back end ASIC which receives processed ultrasound signals and produces ultrasound image data. The image can be displayed on either a standard monitor or on a liquid crystal display (LCD). Comprised as it is of ASICs, the electronics of the unit can be fabricated on a single printed circuit board, eliminating the problems conventionally posed by connectors and cables. This sophisticated ultrasound instrument can be manufactured as a hand held unit weighing less than five pounds.

IN THE DRAWINGS

FIG. 3 is a block diagram of the digital signal processing ASIC of the ultrasound system of FIG. 1;

Figure 1:
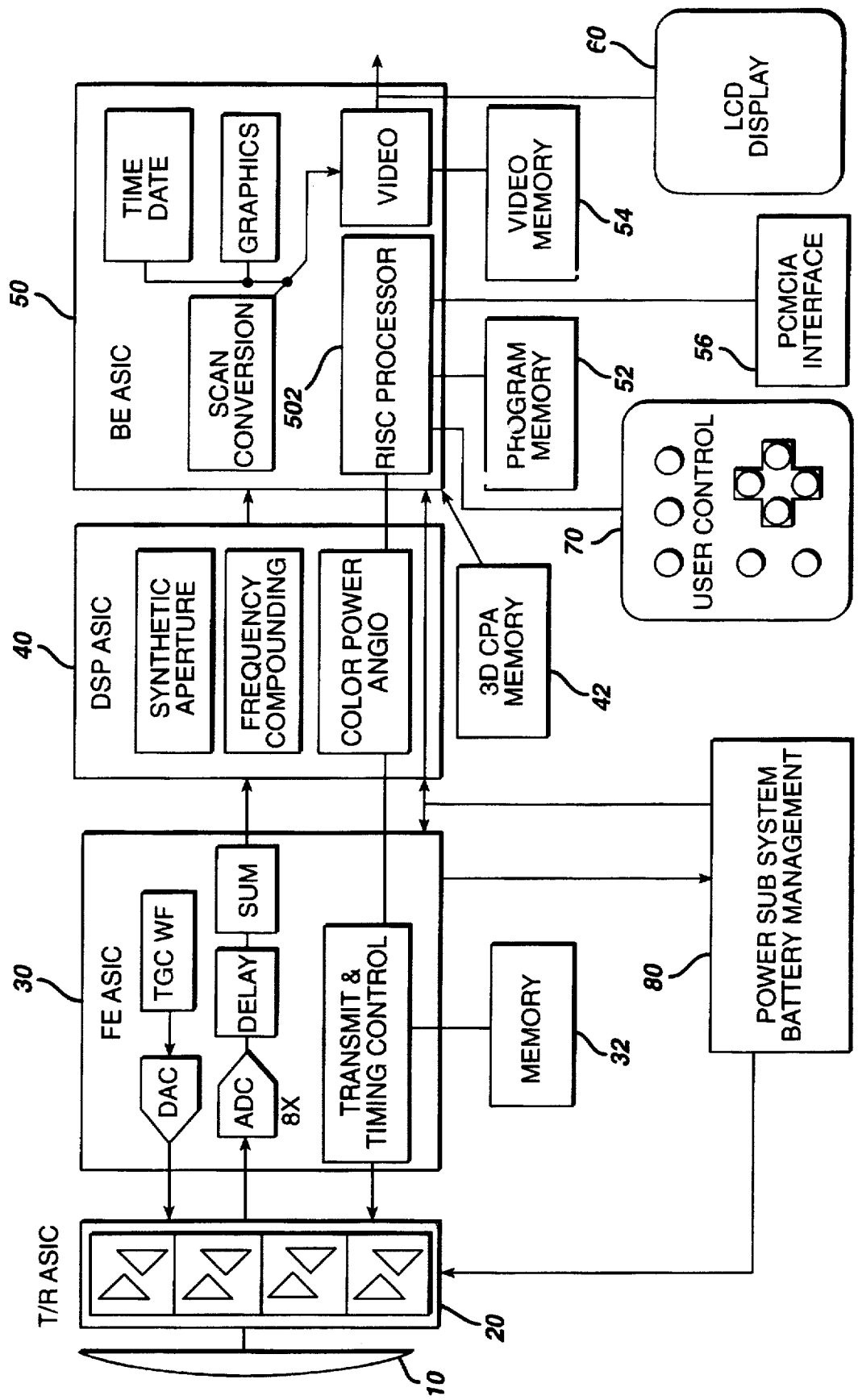
FIG. 1 illustrates in block diagram form the architecture of a hand-held ultrasound system.

Referring first to FIG. 1, the architecture of a hand-held ultrasound system incorporating flash suppression performed in accordance with the principles of the present invention is shown. It is possible to package an entire ultrasound system in a single hand-held unit only through judicious selection of functions and features and efficient use of integrated circuit and ultrasound technology. A transducer array 10 is used for its solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the steering delay requirements on the beamformer. The elements of the array are connected to a transmit/receive ASIC 20 which drives the transducer elements and receives echoes received by the elements. The transmit/receive ASIC 20 also controls the active transmit and receive apertures of the array 10 and the gain of the received echo signals. The transmit/receive ASIC is preferably located within inches of the transducer elements, preferably in the same enclosure, and just behind the transducer. A preferred embodiment of the transmit/ receive ASIC is described in detail in U.S. patent application Ser. No. [ATL-152] filed Apr. 3, 1997 and entitled ULTRASONIC ARRAY TRANSDUCER TRANSCEIVER FOR A HAND HELD ULTRASONIC DIAGNOSTIC INSTRUMENT.

Echoes received by the transmit/receive ASIC 20 are provided to the adjacent front end ASIC 30, which beamforms the echoes from the individual transducer elements into coherent scanline signals. The front end ASIC 30 also controls the transmit waveform timing, aperture and focusing of the ultrasound beam through control signals provided for the transmit/receive ASIC. In the illustrated embodiment the front end ASIC 30 provides timing signals for the other ASICs and time gain control. A power and battery management subsystem 80 monitors and controls the power applied to the transducer array, thereby controlling the acoustic energy which is applied to the patient and minimizing power consumption of the unit. A memory device 32 is connected to the front end ASIC 30, which stores data used by the beamformer. A preferred embodiment of the front end ASIC is described in detail in U.S. patent application Ser. No. [ATL-153] filed May 27, 1997 and entitled HAND HELD ULTRASONIC DIAGNOSTIC INSTRUMENT WITH DIGITAL BEAMFORMER.

Beamformed scanline signals are coupled from the front end ASIC 30 to the digital signal processing ASIC 40. The digital signal processing ASIC 40 filters the scanline signals, processes them as B mode signals, Doppler signals, or both, and in the preferred embodiment also provides several advanced features including synthetic aperture formation, frequency compounding, Doppler processing such as power Doppler (color power angio) processing, and speckle reduction as more fully detailed below.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor 502. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as an infrared transmitter or a PCMCIA interface 56. This interface allows other modules and functions to be attached to or communicate with the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery. Battery power is conserved and applied to the components of the unit from the power subsystem 80. The power subsystem 80 includes a DC converter to convert the low battery voltage to a higher voltage which is applied to the transmit/receive ASIC 20 to drive the elements of the transducer array 10.

Figure 2B:
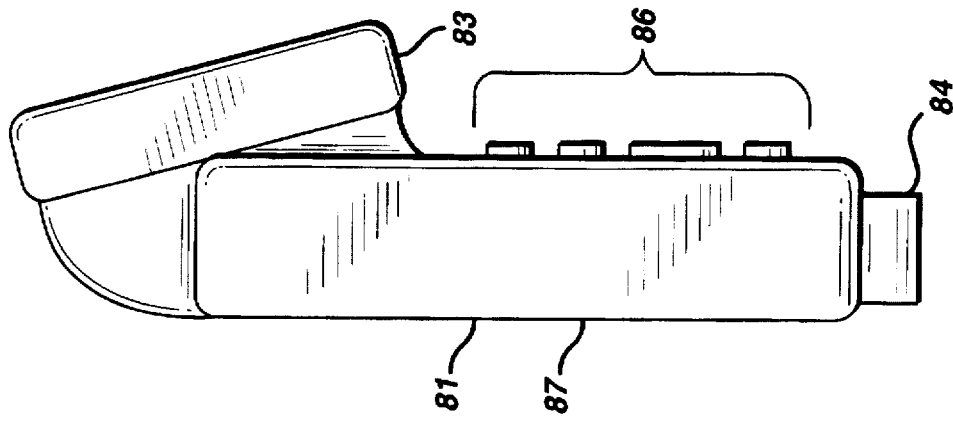
FIGS. 2a and 2b are front and side views of a hand-held ultrasound system which is packaged as a single unit.
Figure 2A:
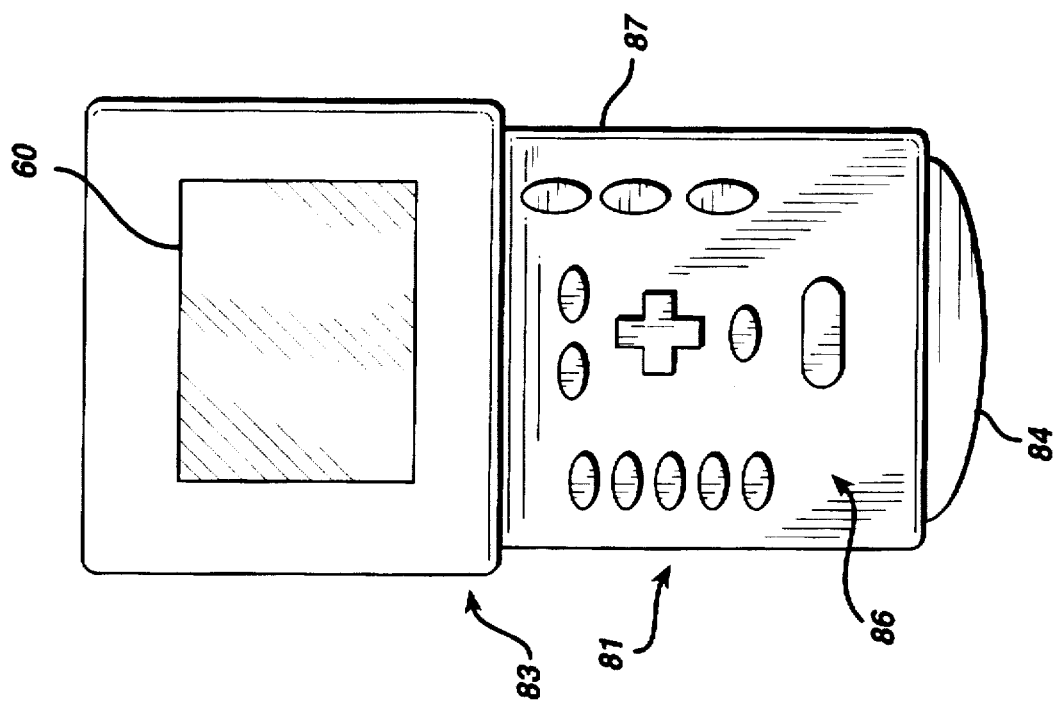

FIGS. 2a and 2b illustrate a one piece unit 87 for housing the ultrasound system of FIG. 1. The front of the unit is shown in FIG. 2a, including an upper section 83 which includes the LCD display 60. The lower section 81 includes the user controls as indicated at 86. The user controls enable the user to turn the unit on and off, select operating characteristics such as the mode (B mode or Doppler), color Doppler sector or frame rate, and special functions such as three dimensional display. The user controls also enable entry of time, date, and patient data. A four way control, shown as a cross, operates as a joystick to maneuver cursors on the screen or select functions from a user menu. Alternatively a mouse ball or track pad can be used to provide cursor and other controls in multiple directions. Several buttons and switches of the controls are dedicated for specific functions such as freezing an image and storing and replaying an image sequence from the Cineloop memory.

At the bottom of the unit 87 is the aperture 84 of the curved transducer array 10. In use, the transducer aperture is held against the patient to scan the patient and the ultrasound image is displayed on the LCD display 60.

FIG. 2b is a side view of the unit 87, showing the depth of the unit. The unit is approximately 20.3 cm high, 11.4 cm wide, and 4.5 cm deep. This unit contains all of the elements of a fully operational ultrasound system with a curved array transducer probe, in a single package weighing less than five pounds. A major portion of this weight is attributable to the battery housed inside the unit.

Figure 4:
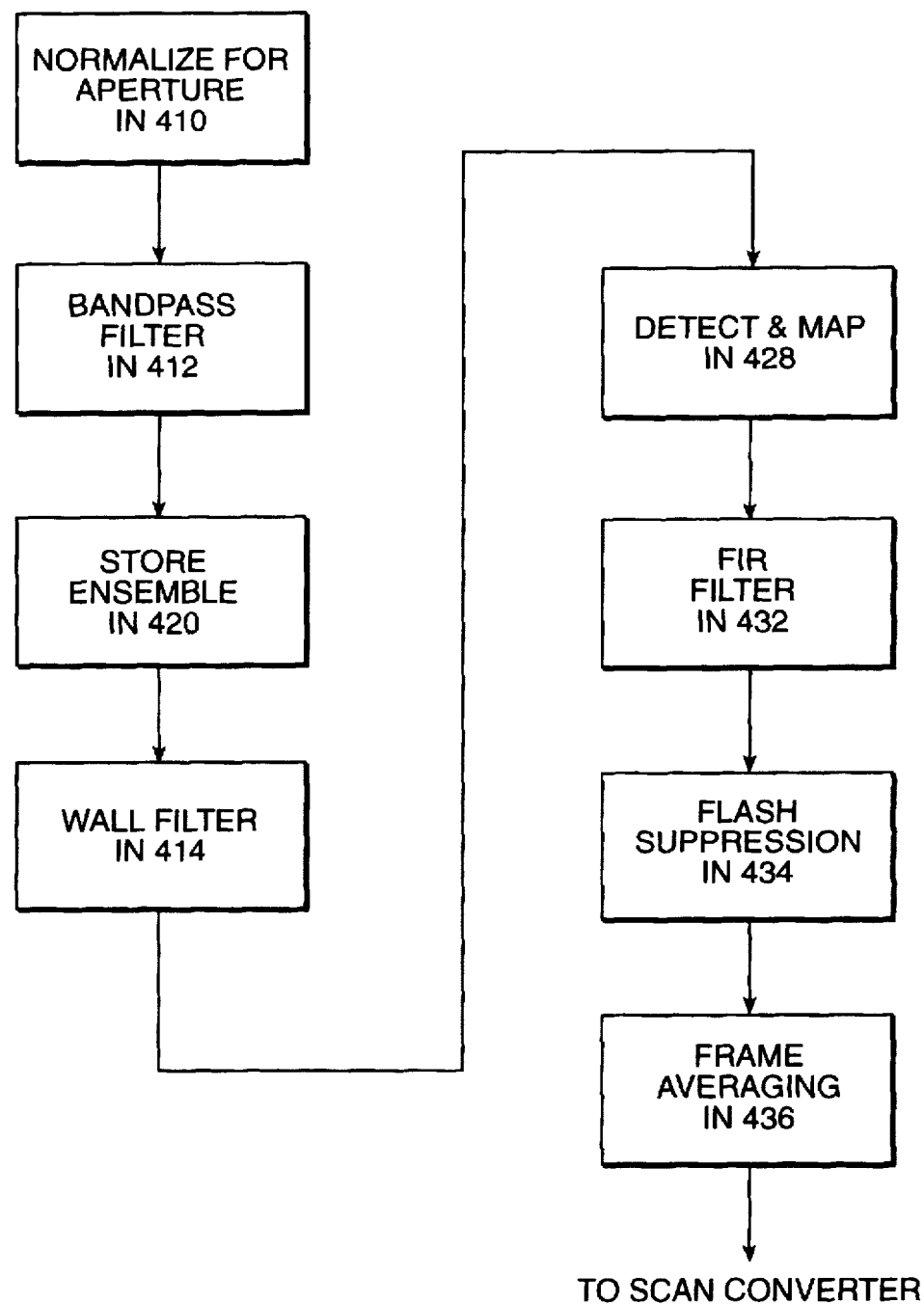
FIG. 4 is a flowchart of Doppler processing by the digital signal processing ASIC.

Referring to FIG. 3, a detailed block diagram of the digital signal processing ASIC 40 is shown. As explained in detail in the parent U.S. patent application, the digital signal processing ASIC performs both B-mode and Doppler signal processing. The processing of Doppler echo signals by the arrangement of FIG. 3 may be understood with reference to the flowchart of FIG. 4. Each scanline location is scanned repetitively, for instance eight times, to assemble an ensemble of Doppler information along the scanline. Each received scanline of echo signals is normalized by the normalization circuit 410 and undergoes decimation band pass filtering in the filter 412. Each scanline of the ensemble is stored in the r.f. memory 420 until a complete ensemble has been accumulated. The scanlines of each ensemble are coupled by the multiplexer 422 to the four multiplier filter 414, which performs wall filtering and Doppler signal estimation through matrix filtering. Wall filtering is performed by selection of appropriate multiplier coefficients and the matrix filtering is of the form $$\begin{bmatrix} y_1 \\ y_2 \\ y_3 \\ \cdot \\ \cdot \\ \cdot \\ y_n \end{bmatrix} = \begin{bmatrix} a_{11} & a_{12} & a_{13} & \cdots & a_{1n} \\ b_{11} & b_{12} & b_{13} & \cdots & b_{1n} \\ c_{11} & c_{12} & c_{13} & \cdots & c_{1n} \\ \cdot & \cdot & \cdot & & \cdot \\ \cdot & \cdot & \cdot & & \cdot \\ \cdot & \cdot & \cdot & & \cdot \\ z_{11} & z_{12} & z_{13} & \cdots & z_{1n} \end{bmatrix} \begin{bmatrix} x_1 \\ x_2 \\ x_3 \\ \cdot \\ \cdot \\ \cdot \\ x_n \end{bmatrix}$$

where $x_1 \ldots x_n$ are spatially aligned signals from the ensemble of scanlines and $y_1 \ldots y_n$ are output Doppler values. The Doppler values are coupled to the detection and compression circuitry 428 through the gain stage 418 and the multiplexer 426, where the Doppler signal amplitude at each echo location along the scanline is detected through absolute value detection of the form $$y = \sum_{n}^{1-n} y_n^2$$

The Doppler values y are compressed and scaled using the CORDIC processor of the detection and compression circuitry 428. The Doppler values are then lowpass filtered by FIR filter 432.

Figure 5:
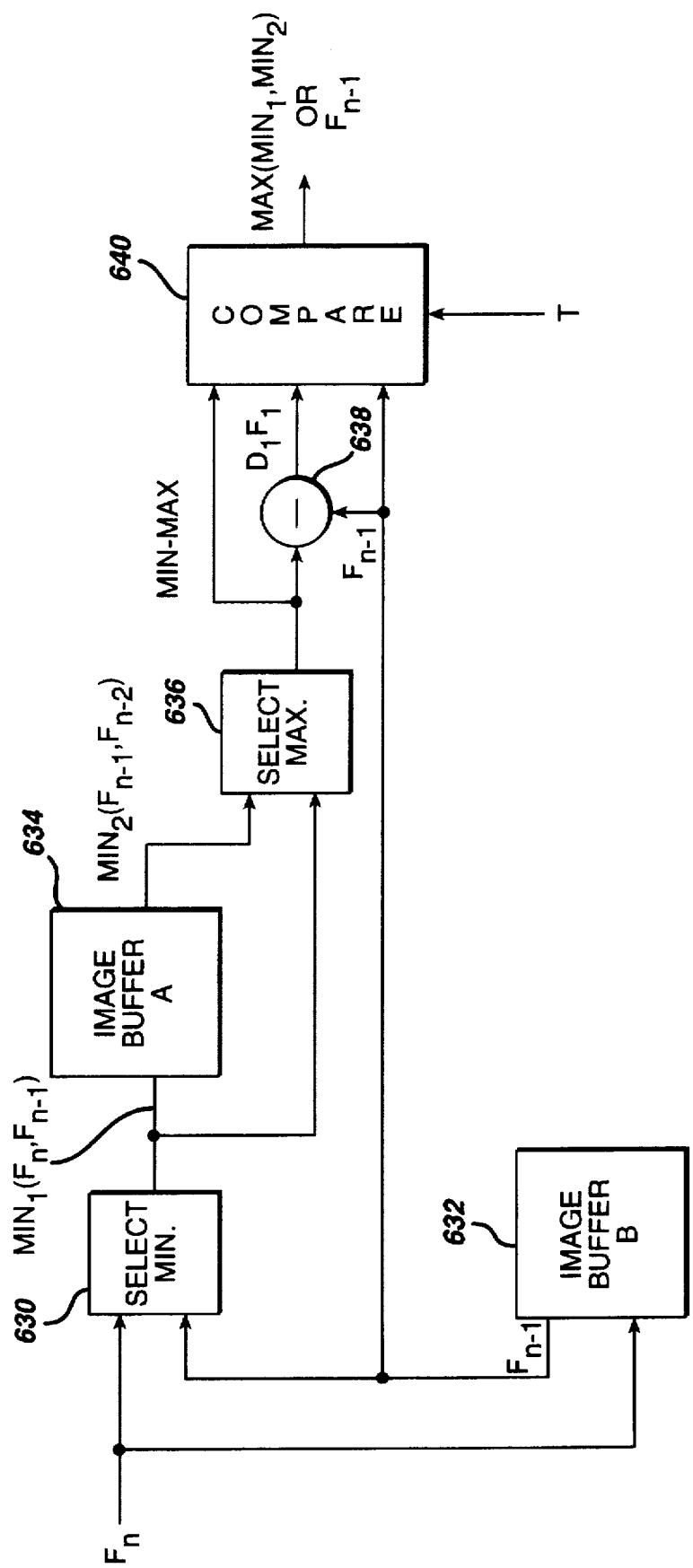
FIG. 5 illustrates a min-max filter for flash suppression constructed in accordance with the principles of the present invention.

In accordance with the principles of the present invention, image clutter is removed from the Doppler signals by a flash suppression processor 434, which eliminates large frame to frame variations in the displayed signals. A preferred technique for flash suppression processing is min-max filtering as shown in the detailed diagram of the flash suppression processor of FIG. 5. Min-max filtering, a class of morphological filtering, is performed on temporal signals from a sequence of Doppler image frames. FIG. 5. illustrates the processing of temporal data at a particular sample volume location, with the frame being processed identified as frame $F_{n-1}$. When the Doppler signal from a new frame $F_n$ is received, it is compared with the value of the previous frame $F_{n-1}$ and the minimum value of the two is selected by a minimum value selector 630. This minimum value $Min_1$ is expressed as $Min_1$ ($F_n, F_{n-1}$). The minimum value $Min_1$ is compared with the previously selected minimum value $Min_2(F_{n-1}, F_{n-2})$ which is stored in an image buffer A, and the maximum of the two values is selected by a maximum value selector 636. The selector 636 therefore selects the maximum of two minimum values, expressed as a min-max value. The min-max value is subtracted from the Doppler signal value of the current frame $F_{n-1}$ by a subtractor 638. A comparator 640 compares this difference against a signal excursion threshold T. If the difference exceed the threshold T, the comparator 640 produces the min-max value for the Doppler signal value of the current frame. If the difference does not exceed the threshold T, the current frame value $F_{n-1}$ is used. When this selection has been made, the $Min_1$ value is latched into the image buffer A in place of the previous $Min_2$ value, new frame value $F_n$ is latched into image buffer B, and the process continues for the other sample volume locations in the current frame, and then the following frame.

This processing may be understood by considering the following sequence (1) of Doppler signal values which are received over time from a given sample volume location:

| 0, 1, 2, 15, 7, 4, 8, 5, 7, 25, 8 | (1) |

Where the first value 0 is of frame $F_n$ and the second value 1 is of frame $F_{n-1}$. When pairs of consecutive values are examined for the minimum of the two, the following sequence (2) of minimum values results:

| 0, 1, 2, 15, 7, 4, 8, 5, 7, 25, 8 | (1) |
| 0, 1, 2, 7, 4, 4, 5, 5, 7, 8 | (2) |

This shows that the minimum of the first two values of the sequence (1), 0 and 1, have a minimum value of 0 which is the first value in the sequence (2). The second and third values of sequence (1), 1 and 2, have a minimum value of 1, the second value in the sequence 2. The third and fourth values of sequence (1), 2 and 15, have a minimum value of 2, the third value in the minimum value sequence (2). Sequential values in the minimum value sequence (2) are then compared to determine the maximum of the two as shown by the min-max sequence (3):

| 0, 1, 2, 15, 7, 4, 8, 5, 7, 25, 8 | (1) |
| 0, 1, 2, 7, 4, 4, 5, 5, 7, 8 | (2) |
| 1, 2, 7, 7, 4, 5, 5, 7, 8 | (3) |

Thus it is seen that the first two values of the minimum value sequence, 0 and 1, have a maximum value of 1, the first value in the min-max sequence (3). The minimum values 1 and 2 have a maximum value of 2, the minimum values 2 and 7 have a maximum value of 7, and so forth.

From the min-max sequence (3) it is seen that the sudden excursions of the fourth, seventh and tenth values of the first sequence, 15, 8, and 25, have been eliminated in the min-max sequence. In the illustrated embodiment the difference between the current value and the min-max value is compared to a threshold and the min-max value used if the difference exceeds the threshold. In this numerical example this difference is the difference between the first and third sequences. If the threshold used is 6, for example, each of the excursions of 15 and 25 would be replaced by min-max values in the processor output. The original values would be used in all other cases.

Figure 6A:
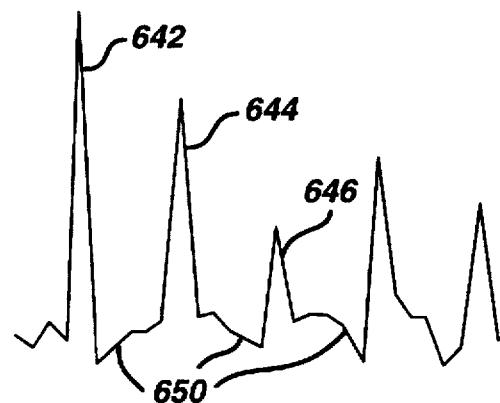
FIGS. 6a–6c are waveforms illustrating the operation of a flash suppression processor of the present invention.
Figure 6B:
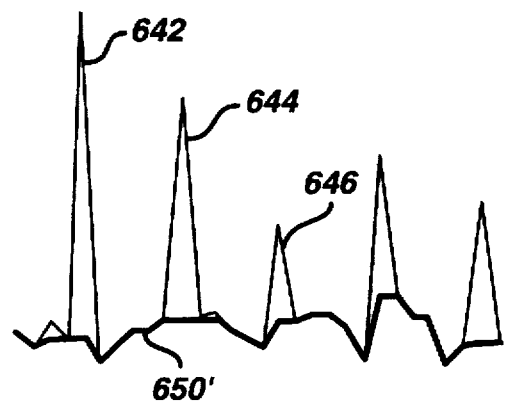
Figure 6C:

Min-max processing as described above will follow the received Doppler signals for signal variations within expected ranges, but will substitute min-max values to smooth over sudden signal excursions, as shown in FIGS. 6a–6c. FIG. 6a shows a sequence 650 of signal values at a given location in a Doppler image. The sequence 650 is contaminated by sudden excursions 642, 644, and 646, which are artifacts from flash (scanhead movement) or other noise sources. The min-max filter of FIG. 5 will substitute min-max values in place of these undesired excursions, as shown by the solid signal sequence 650' below the undesired excursions in FIG. 6b. With the undesired excursions replaced by min-max values, the signal level sequence 650' which is processed for display is as shown in FIG. 6c. A benefit of the min-max processor is that it is effective only for large excursions. The local peaks and valleys which represent the local temporal variations of Doppler power are preserved by this filtering technique.

The foregoing example illustrates a min-max filter with a two-point window. Higher order filters may also be used, such as the following example of a filter with a three-point window for better suppression of consecutive frames with flash artifacts. Suppose that the following sequence of Doppler signal values (4) is received from a sample volume location:

| 0, 1, 2, 15, 7, 4, 8, 5, 7, 25, 8, 5, 6 | (4) |

A three-point window is used to compare these values in groups of three to determine the minimum value of each group, which produces (with the addition of a leading zero value):

| 0, 1, 2, 15, 7, 4, 8, 5, 7, 25, 8, 5, 6 | (4) |
| 0, 0, 1, 2, 4, 4, 4, 5, 5, 7, 5, 5, | (5) |

Now these minimum values are compared in groups of three to determine the maximum of each group, which produces:

| 0, 1, 2, 15, 7, 4, 8, 5, 7, 25, 8, 5, 6 | (4) |
| 0, 0, 1, 2, 4, 4, 4, 5, 5, 7, 5, 5, | (5) |
| 1, 2, 4, 4, 4, 5, 5, 7, 7, 7 | (6) |

It can be seen that the local peak value of 15 and the succeeding high value of 7 have been replaced by values of 4, and that the successive values of 25 and 8 have been replaced with values of 7. The solitary high value of 8 in the middle of the sequence has been replaced with a value of 5, with its preceding and succeeding moderate values of 4 and 5 remaining unchanged.

The response characteristic of the filter can be varied by the threshold of the comparator 640 in the embodiment of FIG. 5, which determines when the original pixel values are to be replaced with min-max values. For example, the values being filtered may have been log compressed in an earlier operation. A threshold of 6 may be used to suppress signal excursions of greater than 6 dB. If values of the original sequence (4) are replaced with values from the min-max sequence (6) only when a threshold of 6 is exceeded, the resulting display sequence will be:

1, 2, 4, 7, 4, 8, 5, 7, 7, 8     (7)

which, like sequence (3), replaces only solitary peak excursions with min-max values.

While the min-max flash suppression filter of the present invention has been illustrated in its preferred useful implementation of a hand-held ultrasound system, it will be appreciated that the filter is effective for removing flash artifacts in any ultrasound system where temporally different Doppler signals can be operated upon on a common spatial basis.

It should also be noted that the inverse operation, max-min filtering, will replace large negative excursions in the same way that min-max filtering replaces large positive excursions. In max-min filtering, the two process steps of the preceding examples are performed in the reverse order, first finding the maximum of successive values, then the minimum of the maximum value sequence. Min-max and max-min filtering can be interchangeable, depending upon the polarity of the undersired excursions. The two operations can also be cascaded in either order, each with its specific comparison threshold, to remove both positive and negative excursions from a sequence of values. For instance, the output of min-max processing can then be max-min processed to eliminate large negative excursions after large positive excursions have first been removed. Processing the in the reverse order will yield the same result.

What is claimed is:

1. A diagnostic ultrasonic imaging system comprising:
   means for receiving Doppler signals which may be contaminated with signal or image artifacts;
   means for filtering said Doppler signals with a min-max filter to remove signal or image artifacts; and
   a Doppler processor for processing said filtered Doppler signals.

2. The diagnostic ultrasonic imaging system of claim 1, wherein said artifacts comprise flash artifacts.

3. The diagnostic ultrasonic imaging system of claim 1, wherein said min-max filter operates upon temporally different Doppler information.

4. The diagnostic ultrasonic imaging system of claim 3, wherein said temporally different Doppler information comprises spatially corresponding Doppler information from temporally different ultrasonic images.

5. The diagnostic ultrasonic imaging system of claim 1, wherein said min-max filter further comprises means for substituting min-max values in place of undesired signal artifacts.

6. The diagnostic ultrasonic imaging system of claim 5, wherein said min-max filter further comprises means for following a received Doppler signal sequence for signal variations within expected ranges, and for substituting min-max values in place of sudden signal excursions.

7. The diagnostic ultrasonic imaging system of claim 1, wherein said min-max filter comprises:
   means for determining the minimum values of a temporal sequence of Doppler data; and
   means for determining the maximum values of said determined minimum values.

8. The diagnostic ultrasonic imaging system of claim 7, wherein said minimum and maximum values are determined from pairs of temporally successive values.

9. In a hand held ultrasound instrument including a transducer for transmitting ultrasonic energy into the body and receiving echo signals from said transmission, a signal processor comprising:
   a motion signal circuit, responsive to said received echo signals for producing a sequence of signals representing motion of substances within the body,
   wherein said motion signal circuit includes a min-max filter for eliminating unwanted signals from said motion signal sequence.

10. In the hand held ultrasound instrument of claim 9, wherein said motion signal circuit produces said sequence of motion signals through Doppler processing, and wherein said unwanted signals comprise flash artifacts.

11. In the hand held ultrasound instrument of claim 10, wherein said sequence of motion signals are grouped in consecutive image frames;
   wherein said min-max filter eliminates flash artifacts by processing spatially corresponding motion signals of a plurality of said image frames.

12. A method for eliminating an unwanted signal from a sequence of spatially corresponding Doppler signals $F_n$, $F_{n-1}$, and $F_{n-2}$ comprising:
   comparing adjacent Doppler signals to find two minimum values $Min_1(F_n, F_{n-1})$ and $Min_2(F_{n-1}, F_{n-2})$;
   identifying the maximum value of said two minimum values; and
   using said identified maximum value to eliminate said unwanted signal.

13. The method of claim 12, wherein the step of using said identified maximum value to eliminate unwanted signal excursions comprises:
   replacing one of said Doppler signals with said identified maximum value.

14. The method of claim 12, wherein the step of using said identified maximum value to eliminate unwanted signal excursions comprises:
   replacing one of said Doppler signals with said identified maximum value if said one of said Doppler signals exceeds a certain level.

15. The method of claim 12, wherein the step of using said identified maximum value to eliminate unwanted signal excursions comprises:
   subtracting said identified maximum value from one of said Doppler signals to obtain a difference value;
   comparing said difference value with a threshold value; and
   replacing said one of said Doppler signals with said identified maximum value when said difference value exceeds said threshold value.

16. A diagnostic ultrasonic imaging system comprising:
   means for receiving Doppler signals which may be contaminated with signal or image artifacts;
   means for filtering said Doppler signals with a max-min filter to remove signal or image artifacts; and a Doppler processor for processing said filtered Doppler signals.

17. The diagnostic ultrasonic imaging system of claim 16, wherein said artifacts comprise flash artifacts.

18. The diagnostic ultrasonic imaging system of claim 16, wherein said max-min filter operates upon temporally different Doppler information.

19. The diagnostic ultrasonic imaging system of claim 18, wherein said temporally different Doppler information comprises spatially corresponding Doppler information from temporally different ultrasonic images.

20. A diagnostic ultrasonic imaging system comprising:

means for receiving ultrasound signals which may be contaminated with signal or image artifacts;

means for filtering said ultrasound signals with a min-max filter to remove signal or image artifacts; and means for filtering said ultrasound signals with a max-min filter to remove signal or image artifacts.

21. The diagnostic ultrasonic imaging system of claim 20, wherein said min-max filter removes artifacts of one polarity, and wherein said max-min filter removes artifacts of an opposite polarity.

22. The diagnostic ultrasonic imaging system of claim 21, wherein said ultrasound signals comprise Doppler ultrasound signals; and further comprising a Doppler processor for processing said filtered Doppler signals.

* * * * *